(12) United States Patent
Bischoff (10) Patent No.: US 8,164,461 B2
(45) Date of Patent: Apr. 24, 2012

(54) MONITORING TASK PERFORMANCE (75) Inventor: Brian J. Bischoff, Red Wing, MN (US)

(73) Assignee: Healthsense, Inc., Mendota Heights, MN (US)

( * ) Notice: Subject to any disclaimer, the term of this patent is extended or adjusted under 35 U.S.C. 154(b) by 273 days.

(21) Appl. No.: 11/788,178

(22) Filed: Apr. 19, 2007

(65) Prior Publication Data

US 2007/0192174 A1 Aug. 16, 2007

Related U.S. Application Data (63) Continuation-in-part of application No. 11/323,077, filed on Dec. 30, 2005.

(51) Int. Cl.
*G08B 23/00* (2006.01)

(52) U.S. Cl. ............... 340/573.1; 340/573.4; 340/573.7; 340/539.11; 340/521; 482/8; 482/9; 434/258

(58) Field of Classification Search ............... 340/573.1, 340/573.4, 573.7, 539.11, 539.12, 539.22, 340/521, 522; 482/8–9; 434/258–261
See application file for complete search history.

(56) References Cited

U.S. PATENT DOCUMENTS

| | | | |
|---|---|---|---|
| 5,447,166 A | 9/1995 | Gevins | |
| 5,724,987 A | 3/1998 | Gevins et al. | |
| 5,810,747 A * | 9/1998 | Brudny et al. | 600/595 |
| 5,890,905 A | 4/1999 | Bergman | |
| 5,905,436 A | 5/1999 | Dwight et al. | |
| 6,042,383 A | 3/2000 | Herron | |
| 6,108,685 A | 8/2000 | Kutzik et al. | |
| 6,281,790 B1 * | 8/2001 | Kimmel et al. | 340/506 |
| 6,402,520 B1 | 6/2002 | Freer | |
| 6,520,905 B1 | 2/2003 | Surve et al. | |
| 6,524,239 B1 | 2/2003 | Reed et al. | |
| 6,540,674 B2 | 4/2003 | Zadrozny et al. | |

(Continued)

FOREIGN PATENT DOCUMENTS

DE 195 22 803 1/1997

OTHER PUBLICATIONS

AIST, Housing That Protects the Home-Maker—Development of Technology Capable of Detecting Abnormalities in the Ordinary Living Pattern Home-Maker for Information Signaling, Feb. 3, 2003.

*Primary Examiner* — Hoi Lau (74) *Attorney, Agent, or Firm* — Brooks, Cameron & Huebach, PLLC (57) ABSTRACT

One system embodiment includes providing a number of sensors for monitoring an individual in performing a number of tasks from a list of tasks to be completed, the number of tasks each including, an associated number of steps to be completed by the individual, monitoring the performance of a task from the list by using at least one of the number of sensors, providing the individual with a number of step instruction prompts associated with the steps of the task, and obtaining task performance information corresponding to the performance of the task by the individual. The task performance information includes step prompt information including the number of step instruction prompts provided during performance of the task, sensor data from the at least one of the number of sensors, and adjusting the list of tasks to be completed based on the task performance information of the task.

33 Claims, 5 Drawing Sheets

U.S. PATENT DOCUMENTS

| | | |
|---|---|---|
| 6,558,165 B1 | 5/2003 | Curry et al. |
| 6,626,676 B2 | 9/2003 | Freer |
| 6,821,258 B2 | 11/2004 | Reed et al. |
| 6,950,026 B2 | 9/2005 | Yamashita et al. |
| 2002/0198473 A1 | 12/2002 | Kumar et al. |
| 2003/0004652 A1 | 1/2003 | Brunner et al. |
| 2003/0114736 A1 | 6/2003 | Reed et al. |
| 2003/0117279 A1 | 6/2003 | Ueno et al. |
| 2003/0130590 A1 | 7/2003 | Bui et al. |
| 2003/0185436 A1* | 10/2003 | Smith .......................... 382/159 |
| 2003/0189485 A1 | 10/2003 | Smith |
| 2003/0216670 A1* | 11/2003 | Beggs .......................... 600/595 |
| 2003/0229471 A1 | 12/2003 | Guralnik et al. |
| 2003/0236451 A1* | 12/2003 | El-Nokaly et al. ............ 600/300 |
| 2004/0131998 A1 | 7/2004 | Marom et al. |
| 2004/0191747 A1* | 9/2004 | Atsumori et al. ............. 434/323 |
| 2004/0219498 A1* | 11/2004 | Davidson ..................... 434/247 |
| 2005/0024199 A1* | 2/2005 | Huey et al. ................... 340/521 |
| 2005/0057357 A1* | 3/2005 | Helal et al. ............... 340/539.13 |
| 2005/0065452 A1* | 3/2005 | Thompson .................... 600/558 |
| 2005/0073391 A1* | 4/2005 | Mizobuchi ................... 340/5.74 |
| 2005/0131736 A1 | 6/2005 | Nelson et al. |
| 2005/0137465 A1* | 6/2005 | Cuddihy et al. ............. 600/300 |
| 2005/0244797 A9 | 11/2005 | Klingberg |
| 2005/0264425 A1* | 12/2005 | Sato et al. ................... 340/573.1 |
| 2006/0161218 A1* | 7/2006 | Danilov ......................... 607/45 |
| 2007/0032738 A1* | 2/2007 | Flaherty et al. ............... 600/545 |
| 2007/0132597 A1* | 6/2007 | Rodgers ..................... 340/573.1 |
| 2007/0152837 A1* | 7/2007 | Bischoff et al. ............ 340/573.1 |

* cited by examiner

MONITORING TASK PERFORMANCE

CROSS-REFERENCE TO RELATED APPLICATIONS

This application is a continuation-in-part of U.S. application Ser. No. 11/323,077, filed Dec. 30, 2005.

BACKGROUND OF THE DISCLOSURE

Methods, devices, and systems have been developed in various fields of technology for the monitoring of the movement and/or health of an individual. With respect to the monitoring of the health of an individual, some methods, devices, and systems have been developed to aid in the diagnosis and treatment of individuals.

In the field of remote health monitoring, for instance, systems have been developed to enable an individual to contact medical professionals from their dwelling regarding a medical emergency. For example, in various systems, a system is equipped with an emergency call button on a base station that initiates a call or signal to an emergency call center from a user's home telephone. The concept of such a system is that if an individual has a health related problem, they can press the emergency call button and emergency medical providers will respond to assist them.

To aid in situations, such as where an individual has fallen and cannot reach an emergency call button on the base station, mobile devices have been developed. The mobile devices generally include an emergency call button that transmits a signal to the base station in the dwelling indicating an emergency. Once the signal is made, the base station alerts a remote assistance center that can contact emergency medical personnel or a designated third party.

Systems have also been developed that use sensors within the home to monitor an individual within a dwelling. Typically, these systems include motion sensors, for example, that are connected to a base control system that monitors areas within the dwelling for movement.

In such systems, when a lack of movement is indicated, the system indicates the lack of movement to a remote assistance center that can contact a party to aid the individual. Additionally, such sensing systems also monitor the health of the system, and its sensors, based upon the individual sensor activations.

With respect to diagnosis and treatment, some systems can be used to diagnose and/or improve brain functionality. For example, in one system, the individual uses a computing program that goes through a number of exercises on the display of the computing device.

In such systems, the individual makes a selection from one of a number of choices presented on the display and executable instructions within the computing device determine whether the answer is correct. Such systems can aid in recovery of memory that has been lost due to a traumatic brain injury or can aid in relearning such information, among other uses.

Additionally, some systems can include functionality that aids the individual in their daily routine. For example, some systems can provide a scheduling functionality that can utilize reminders directed to an individual that may have reduced brain functionality.

In this way, the individual can continue with a daily routine, through the use of prompts from a computing device with such scheduling functionality, even though the individual may not know what they are supposed to do next. Further, such systems can also aid in recovery of memory that has been lost due to a traumatic brain injury or can aid in relearning such information, among other uses.

DETAILED DESCRIPTION OF THE DISCLOSURE

Embodiments of the present disclosure can provide simple, cost effective, privacy-respecting, and/or relatively non-intrusive methods, devices, and/or systems for monitoring task performance. Embodiments of the present disclosure, for example, can be utilized with and can include systems and devices as described in U.S. application Ser. No. 11/323,077, filed Dec. 20, 2005. The present disclosure provides detail into task performance concepts that can be used with the systems discussed in the above referenced application, the present application, and/or other systems for monitoring one or more individuals.

For instance, embodiments can include systems, methods, and devices to monitor the activity of an individual within or around a dwelling. As used herein, a "dwelling" can, for example, be a house, condominium, townhouse, apartment, or institution (e.g., hospital, assisted living facility, nursing home, prison, etc.). Embodiments, for example, can monitor the task performance of an individual within or around a dwelling.

For example, an embodiment can use a fixed or mobile device to aid an individual in performing a kitchen function, such as making lunch, or opening a drawer, among other functions. Various embodiments can be designed such that, based upon a number of task performance factors, when an individual is successfully completing a task that information can be evaluated to determine whether the difficulty of the task, when repeated, and/or the whether the difficulty of the next task, can be adjusted to better fit the individual and/or can be adjusted to challenge the individual being monitored.

Various embodiments can include systems, methods, or devices that utilize a fixed or mobile device to monitor activity of an individual within and/or out of a dwelling, such as monitoring the task performance of an individual. For example, in some embodiments, a mobile device can be used to aid an individual in running errands, among other functions.

To monitor the activity of an individual, various embodiments can provide automated detection of changes in activity within a dwelling and automated initiation of alerts to third parties to check on and/or assist the individual where assistance is needed, thereby avoiding prolonged periods of time before assistance is provided. Some embodiments can utilize multiple sensors, multiple timers, and/or multiple rules to determine whether to initiate an action, thereby increasing the certainty that an action is necessary and should be initiated. Various embodiments also can utilize multiple sensors, multiple timers, and/or multiple rules to make statistical correlations between a number of sensors, thereby increasing certainty that the system is in satisfactory health.

In some embodiments, the logic component can be rules-based, and can initiate a timer which establishes a time period for making the determination. The system can then monitor sensors within the dwelling to determine whether a particular task has been completed. For such review, the system can include memory to store such information or send the information to a remote server (e.g., at a remote monitoring site), for example.

A system embodiment can, for example, include providing a number of sensors for monitoring an individual in performing a number of tasks from a list of tasks to be completed. The number of tasks can be large items, such as a list of errands to be accomplished in a given day, and/or can be small items, such as the steps for taking a bath.

The level of detail of the tasks provided to the individual can be determined in a number of ways. For example, in some embodiments, the level of detail can be determined by the manufacturer, a system installer, a system administrator, a care provider, and/or the individual being monitored.

Additionally, in some embodiments, the system (e.g., through use of executable instructions executed by logic component) can set the level of detail of the tasks presented to an individual. In some embodiments, the level of detail can be adjustable based upon one or more factors including, but not limited to, length of time that the individual has been monitored, number of times a particular task has been performed, success rate of task performance, and/or percentage of correct steps versus incorrect steps in performing a task, among other factors. Embodiments can be designed such that the number of tasks or steps can be increased and/or decreased based upon such factors.

As discussed above, a task can include an associated number of steps to be completed by an individual. In some embodiments, each task can include multiple steps.

In various embodiments, the performance of a task from a list of tasks can be monitored by using at least one of a number of sensors. This can be accomplished, for example, by waiting for a sensor response that indicates that the task has been performed, such as pressing a button when done, or inferring that a task has been accomplished based upon the feedback provided by the sensors.

For example, regarding the task of brushing teeth, the system can be designed such that sensors sense the opening of a drawer containing the toothpaste and toothbrush, sensors detecting the water being turned on and off, and sensors detecting the drawer being closed. Such sensor feedback can infer that the user has opened a drawer, removed the toothpaste and toothbrush, run the water to rinse, and returned the toothpaste and brush to the drawer. Such routines can be pre-selected and provided as executable instructions provided in the system and displayed for the individual to follow and/or can be designed based upon the individual's routine and entered before system installation, at system installation, and/or after installation.

In using such routines, the individual can be provided with a number of step instruction prompts associated with the steps of the task. These prompts can be short prompts that indicate a brief instruction to the individual, such as open drawer, or can have a lot of information, such as, "You are now going to brush your teeth. Take your brush and paste out of the drawer, add paste to brush, place brush in mouth and start brushing motion, rinse mouth with water, and place brush and paste back in drawer."

Such level of detail of prompts can be determined and provided before system installation, at system installation, and/or after installation, in various embodiments. These prompts can be provided in various formats, such as text, image, video, and/or audio.

Task performance information corresponding to the performance of the task by the individual can be obtained by the system. Such information can be obtained via the sensors which can include direct or inferred information, as discussed above.

Task performance information can include step prompt information including the number of step instruction prompts provided during performance of the task, sensor data from the at least one of the number of sensors, and adjusting the list of tasks to be completed based on the task performance information of the task, in various embodiments.

In some embodiments, announcements can be provided to the individual. These announcements can provide any suitable information to the individual. For example, an announcement can be provided for accomplishment of a step or task, in various embodiments.

In some embodiments, adjusting the list of tasks can include changing the number of tasks from the list of tasks to be completed. Adjusting the list of tasks can additionally, or alternatively, include changing the number of steps associated with one or more particular tasks.

In various embodiments, the embodiment can include prompting the individual to perform a second task from the list when the first task has been completed. In some embodiments, prompting the individual can be accomplished via a mobile device.

Providing the individual with a number of step instruction prompts can include providing the individual with a reminder when a step of the first task remains uncompleted. This can aid in encouraging the individual to finish an unfinished task.

Some embodiments can include scheduling the number of tasks to be completed by the individual. For example, the number of tasks to be completed can be provided in a sequential order, among other ordering formats.

In some embodiments directed to a method for monitoring task performance, the method can include providing a number of sensors for monitoring the individual in performing a number of tasks from a list of tasks to be completed. The number of tasks can each include, for example, an associated number of steps to be completed by the individual, initiating a first task having an associated number of steps based upon one or more context items, monitoring the performance of the first task by using at least one of the number of sensors, and/or providing a task completion indication based upon a determination of completion of the first task.

Initiating the first task based upon one or more context items can include initiating the first task based upon one or more context items from the group including a time of day, a day of the week, a list of completed tasks, a list of uncompleted tasks, a completion status of a particular task, and/or a determined location of the individual, among other items.

Initiating the first task based upon one or more context items can include initiating the first task based upon localizing the individual within a residence by using at least one fixed sensor located in the residence. For example, motion sensors can be used to locate and individual.

Other types of sensors can be used. For example, an individual can be located based upon an activation of one or more sensors (e.g., Activation of a number of sensors in the kitchen can be an indication of the location of the individual. In some embodiments, the certainty can be increased by evaluating a combination of both fixed and wearable sensors to verify whether the individual is in the kitchen). The combination of fixed and wearable sensors can be used to improve the accuracy of the location detection and to distinguish between multiple individuals in the dwelling.

Some embodiments can include monitoring the performance of the first task by using at least one of a number of fixed sensors and by using at least one portable sensor worn by the individual. Monitoring the performance of the first task can also include using the at least one portable sensor to determine whether the first task is being completed.

Initiating the first task can include prompting the individual on an interface of a mobile device, in some embodiments. In various embodiments, the first task can be initiated based upon integrating sensor data provided by at least one fixed sensor and at least one portable sensor.

Some embodiments can include initiating a second task having an associated number of steps to be completed based upon one or more context items. Such context items will be discussed in more detail herein.

In various embodiments, a method can include monitoring the performance of the first task by using integrated sensor data provided by at least one fixed sensor and at least one portable sensor. For example, the position of the individual can be ascertained by the location of the portable sensor and the fixed sensor can indicate what the individual is doing (e.g., opening a drawer).

The present disclosure also provides a number of system embodiments. For example, a system embodiment for monitoring task performance can include a number of fixed sensors located throughout a residence of the individual. In some such systems, a number of portable sensor can be worn or carried by the individual.

A computing device can be used to communicate with a number of fixed sensors and the portable sensors. Computing devices can include memory having instructions storable thereon and executable by a processor or other logic component to perform a method.

An example of a method can include monitoring, by using one or more sensors, the performance of a first task from a list of tasks to be completed. Each of the tasks can include an associated number of steps to be completed by the individual.

In some embodiments the individual can be provided with a number of step instruction prompts corresponding to an associated number of steps of a first task. Task performance information can be obtained that corresponds to the performance of the first task by the individual. This task performance information can include, for example, step prompt information including the number of step instruction prompts provided during performance of the first task, and/or sensor data from the at least one of the number of sensors, indicating that a particular step has been completed based on the sensor data. Based on the task performance information corresponding to the performance of the first task, the number of step instruction prompts provided to the individual in performing the first task on a subsequent occasion can be adjusted. This can be beneficial in continuing to challenge the individual and in tailoring the system to the learning speed and/or granularity of the individual.

In various embodiments, the system can be designed to indicate whether a step or task has been completed. This can be accomplished in a variety of manners and can be presented to the individual or can be transparent to the individual. For example, indicating that a particular step has been completed can be accomplished by placing a flag in a data file and/or by an announcement to the individual.

The adjustment of the number of step instruction prompt can be accomplished in a number of ways. For example, adjusting the number of step instruction prompts provided to the individual in performing the first task on a subsequent occasion can be accomplished via a user interface (e.g., a health professional, system administrator, etc.) and/or via an interface usable by the individual being monitored. Adjusting the number of step instruction prompts provided to the individual in performing the first task on a subsequent occasion be accomplished by increasing or reducing the number of step instruction prompts provided to the individual in performing the first task on the subsequent occasion.

In various embodiments, a system can include instructions to analyze the task performance information and to initiate adjusting the number of step instruction prompts provided to the individual in performing the first task on a subsequent occasion. In some embodiments, a system can include one or more instructions to schedule the number of tasks to be completed by the individual. Such systems can include a guidance module for providing guidance information for accomplishing at least one step. System embodiments can include a tracking module for tracking completion of the steps associated with at least one task.

Additionally, in some embodiments, the system can include an emotion sensing module. Such a module can be helpful, for example, in determining if the individual is getting frustrated with a particular situation and needs some assistance or a prompt.

In various embodiments, the system can include a solution module to provide information to the individual that may aid in solving a particular problem encountered by the individual. The solution module can, for example, include instructions executable to assist the individual with locating a particular item by providing the individual with a number of possible locations of an item. In such embodiments, the number of possible locations can, for example, be based on data from at least one of the number of fixed sensors and/or based on data from a database, among other data locations.

Figure 1:
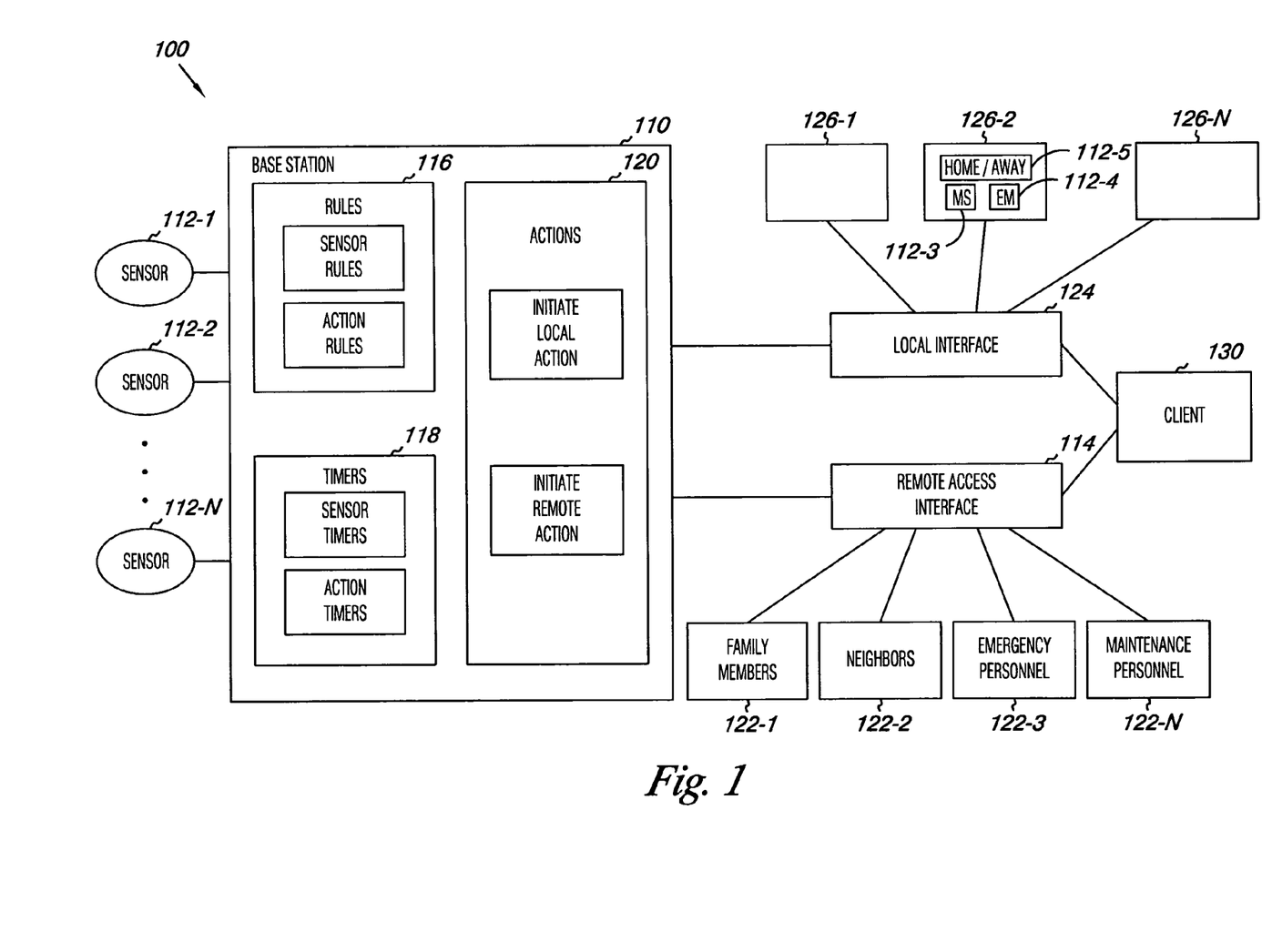
FIG. 1 illustrates a monitoring system embodiment.

FIG. 1 illustrates a monitoring system embodiment. The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of value.

In the illustrated embodiment of FIG. 1, the system 100 utilizes the base station 110 to monitor the activities of a client (e.g., an individual) in and/or around a dwelling through use of a number of sensors 112-1, 112-2, and 112-N. The number of sensors can be a number of fixed or portable sensors.

Monitoring the performance of a particular task can include using at least one portable sensor to determine whether the task is being completed. These determinations can be responses to a prompt made by the system, or can be inferred based upon the individual's daily activities as sensed by one or more sensors.

In such embodiments, the system can prompt an individual for a specific response and/or can determine whether a task has been accomplished based upon the activity of the individual. For instance, a system can be designed to ask the individual if the individual has brushed his teeth and the individual can respond to the system with a response that indicates yes (e.g., closing the drawer holding the tooth brush, pressing a button on a mobile or fixed device, or an audible response identified by an audio sensor).

The base station 110 can also initiate a number of actions based upon a number of rules implemented by the base station 110. These rules use the information obtained from the number of sensors 112-1 through 112-N to determine whether to initiate an action or not. For example, a rule may be that if a yes response is received, go to the next task on a task list.

The base station 110 includes a number of components providing a number of functions, as will be discussed herein. In the embodiment of FIG. 1, the base station 110 is illustrated with respect to its various functionalities. For example, the base station 110 is capable of using rules 116 and/or timers 118 to determine whether to initiate an action 120.

As discussed herein, in some embodiments the base station 110 includes executable instructions to receive signals from sensors 112-1 through 112-N that are generated by activation of a sensor 112-1 through 112-N. Embodiments of the disclosure can include various types of sensing devices, including on/off type sensors, and/or ones whose signal strengths scale to the size of the activation parameter, such as temperature, weight, or touch.

The one or more sensors can be of many different types. For example types of sensors can include, but are not limited to, sensors to indicate the opening and closing of a door and/or drawer; sensors to indicate the movement of objects such as shades and/or blinds; current and/or voltage sensors to monitor appliances, lights, wells, etc.; pressure or fluid flow sensors to indicate the turning on and off of water; temperature sensors to indicate that the furnace is on or off; force sensors such as strain gauge sensors to sense an individual walking over a pad, sitting in a chair, or lying in bed; motion sensors to sense the motion of objects within the dwelling; alert switches/buttons to signal an emergency or client input such as a cancellation request; and sensors to measure the signal strength between multiple sensors. Sensors may also include those carried or worn by the individual, such as, vibration, temperature, audio, touch, humidity, Electro Cardio Gram (ECG), Electro Encephalogram (EEG) and/or Resistance (e.g., Galvanic Skin Reaction, etc.), among other well know sensing devices.

A sensor can also be a button on the base station 110 and/or mobile device 126-2 which senses when someone actuates the button. Sensors can be analog and/or digital type sensors and can include logic circuitry and/or executable instructions to transmit signal output to the base station 110.

In some embodiments, the base station 110 can utilize a remote assistance center device (indicated as Remote Access Interface) 114 to inform a third party 122-1 through 122-N that an alert condition exists and that aid may be needed. Aid can be a call to the individual 130, a visit by a third party 122-1 through 122-N to the location of the individual 130, or other such aid. As used herein, "third parties" 122-1 through 122-N can include hospital staff, emergency medical technicians, system technicians, doctors, neighbors, family members, friends of the individual 130, police, fire department, and/or emergency 911 operators.

In the embodiment of FIG. 1, the base station 110 and the remote assistance center device 114 can each be any type of computing device capable of managing the functionality of receiving alert requests and initiating such requests. For example, suitable devices can include personal computers, mainframe computers, system servers, devices having computer components therein, and other such devices.

As illustrated in FIG. 1, the remote assistance center device 114 and a local interface 124 are accessible by an individual 130 (e.g., client). The communication between the devices 110, 112-1 through 112-N, and 124 can be accomplished in various manners.

For example, in the embodiment shown in FIG. 1, the communications can be accomplished by wired (e.g., telephone lines) and/or wireless (e.g., radio interface) communications. Further, in some embodiments, the functionality of these devices can be provided in fewer devices than shown, or in more devices than shown.

In an additional embodiment, system devices 126-1 through 126-N (where "N" represents any number) can also communicate with the base station 110 through the local interface 124. In some embodiments, a system device can be in the form of a mobile device 126-1. The mobile device 126-1 can, in some embodiments, provide access to and/or control of at least some of the functions of the base station 110 described herein. Embodiments of the mobile device 126-1 are discussed in greater detail herein.

In some embodiments, a logic component can be used to control the functions of the base station 110. For example, the logic component can include executable instructions for providing such functions as handling received information from the sensors in the system, time-stamping received information such as sensor activation and/or system health functionality, among others. In some embodiments, the logic component can include RAM and/or ROM, a clock, an input/output, and a processor, among other things.

In some embodiments, a mobile device can be used with the base station 110. The mobile device can be carried or worn by the individual 130, as discussed herein. Mobile devices 126-2 can be any type of device that is portable and that can provide the described functionalities.

Examples can include basic devices that have the capability to provide such functionalities, up to complex devices, having multiple functions. Examples of complex mobile devices 126-2 can include mobile telephones and portable computing devices, such as personal digital assistants (PDAs), and the like.

In some embodiments, the mobile device can have home/away functionality to indicate whether the individual 130 is within a certain distance of the base station 110 of the system, for instance, through use of a sensor (e.g., sensor 112-5). In some embodiments, a transceiver, transmitter, and/or receiver can be used to transmit signals to and/or receive signals from the base station 110 within the dwelling.

As used herein, a transmitter and a transceiver can be used interchangeably if a transmission functionality is desired. Additionally, a receiver and a transceiver can be used interchangeably if a reception functionality is desired.

For example, a short range communication type of communication can be used. Short range communication types of sensors can include IEEE 802.15.4 and/or IEEE 802.11 protocols, among others.

As discussed herein, the mobile device 126-2 can communicate with the base station 110 using short range communication signals. In these embodiments, the mobile device 126-2 can use a short range communication signal and the local interface 124 can be incorporated into the base station 110.

Additionally, in some embodiments, the mobile device 126-2 can utilize a long range communication signal to communicate to the base station 110. In these embodiments, the local interface 124 can be a mobile device such as a mobile telephone that can send the instructions from the mobile device 126-2 to the base station 110. In such embodiments, the mobile device 126-2 can be separate from, associated with, or included in the mobile telephone.

Additionally, the mobile device can include executable instructions to enable the mobile device 126-2 to communicate with the mobile telephone in order to instruct the mobile telephone how to forward its base station message to the base station 110. In some embodiments, the base station 110 can include executable instructions to enable a short range communication signal to be translated into a long range wireless signal.

In an additional embodiment, the number of sensors 112-1 through 112-N can include a task sensor, where the task sensor is associated with a task assigned to the individual 130. For example, in some embodiments the individual 130 is assigned the task of retrieving a beverage.

In such embodiments, the task sensor would be the sensor that is activated when the refrigerator door is opened. The logic component can thus be designed to couple the task to the task sensor and to initiate a task-complete action when the task sensor is activated. In some embodiments, the task-complete action can be to send a signal to the remote assistance center device that the task was completed successfully.

Other task-complete actions may also be taken. In some embodiments, one or more sensors can be used to identify when a task is compete and/or in progress. Such embodiments can accomplish these tasks, for example, by monitoring the actuation of one or more sensors, the time between sensor activations, and other such suitable manners.

In some situations, more than one individual 130 being monitored lives inside a single dwelling. In this situation, the home/away sensor 112-5 and/or mobile device 126-2 can be equipped with an identification tag. In some embodiments, the logic component can be designed to initiate a task-complete action when the task sensor is activated and when the signal strength between the home/away sensor 112-5 with the correct identification tag is larger than the signal strength between the home/away sensor 112-5 with a different identification tag and the task sensor.

As discussed herein, the mobile device can be equipped with components including, but not limited to, a display, a transceiver, a transmitter and/or a receiver, an antenna, a power source, a microprocessor, memory, input devices, and/or other output devices such as lights, speakers, and/or buzzers.

In addition, in some embodiments, the mobile device can include an "awaken" mechanism, where activating the awaken mechanism transmits a wireless signal indicative of a return of the mobile device to within the base range of the base station. When the awaken mechanism is activated, the mobile device can begin to send signals to the base station at the first predetermined amount of time if five (5) seconds at the first predefined time interval of thirty (30) seconds. Other first and second predetermined times of signal length and first and second predefined time intervals are also possible.

In some embodiments, the mobile device can be constructed to periodically check-in with the base station device, such as by sending a ping signal to the base station device via radio frequency or other such manner. In such embodiments, the mobile device can be provided with energy saving executable instructions that allow the mobile device to be in "sleep mode," where power usage is reduced, and then to "awaken" periodically to send a ping signal to the base station device.

Once the signal is sent, the mobile device can then return to "sleep mode." When in "sleep mode" the client can awaken the mobile device manually, for instance, by pushing an emergency button.

Figure 2:
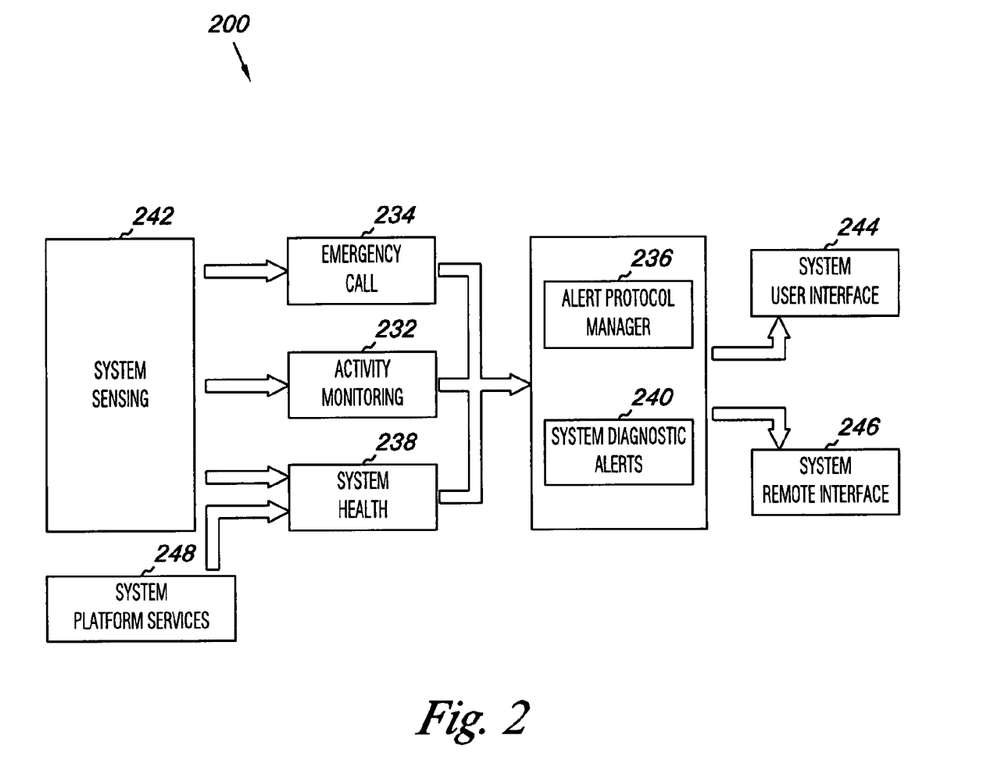
FIG. 2 illustrates an embodiment of base station data flow.

FIG. 2 illustrates an embodiment of base station data flow. This diagram illustrates the flow of information from various parts of the system. In the embodiment shown in FIG. 2, the system sensing information 242 can be used in a variety of functions provided by the system 200.

For example, system sensing information can be used to support emergency call functions 234, activity monitoring functions 232, and system health functions 238, among others. Each of these functions (i.e., 232, 234, and 238) utilizes information about either a sensor or an activity of an individual that activates a sensor.

The blocks 232, 234, and/or 238 can process and interpret information from system sensing block 242 in order to provide information to the alert protocol manager functionality 236, and a system diagnostic alert protocol functionality 240. These functionalities can be provided at the base station and/or at a remote location, for example. Individually, blocks 232, 234, or 238 can pass system information directly to the alert protocol manager 236, or can process the information itself to determine the need to initiate an alert request or other action request to the alert protocol manager 236.

The alert protocol manager 236 can initiate an alert upon a request from 232, 234, or 238, or can further process the information received from 232, 234, or 238 to determine whether to initiate an alert or other action.

In the embodiment illustrated in FIG. 2, the initiation of an alert by the alert protocol manager 236 can be implemented through use of functions within the system client interface 244 and/or the system remote interface 246. In various embodiments, the system remote interface 246 can be a call center computer, such as a computer at an emergency call center. For example, an alert process can include a notification of the client that an alert will be or has been initiated.

This can be brought to the client's attention to allow the client to cancel the alert if the need for an intervention does not exist or has passed. In such cases, the system client interface can be used to indicate the impending or existing alert condition and/or can be used by the client to confirm and/or cancel the alert.

The system remote interface can be used to contact a third party, such as a remote assistance center device to inform the third party that an alert condition exists and that aid may be needed. Aid can be a call to the client of the system, a visit by a third party (e.g., doctor, emergency medical personal, system technician, etc.) to the location of the client, or other such aid, as discussed herein.

Similarly, system information can be provided from the system platform services block 248 to the system health block 238. This information can be used to determine whether to issue an alert for a fault in the system, for a software/firmware update, or the like. The system diagnostic alert block 240 can be used to issue such an alert. This alert can then be effectuated through the system client interface 244 and/or the system remote interface 246.

For example, if a sensor has to have a battery changed, the alert can be sent to both the individual and a third party (e.g., via blocks 244 and 246). If the client changes the battery, the alert can be canceled and notification of the cancellation can be provided to the third party.

Although embodiments illustrated herein may indicate a flow path, this is meant to be an example of flow and should not be viewed as limiting. Further, unless explicitly stated, the embodiments described herein are not constrained to a particular order or sequence. Additionally, some of the described embodiments and elements thereof can occur or be performed at the same point in time. Embodiments can be performed by executable instructions such as software and/or firmware.

Various embodiments can include different types of activity monitoring alert protocol management. Activity monitoring alert protocol management functionality can be accomplished by a number of executable instructions and/or through use of logic circuitry.

Further, in various embodiments, the executable instructions and/or, in some embodiments, the logic of the mobile device can be updated. For example, this can be accomplished wirelessly via communication with the base station, among other updating methods.

Figure 3:
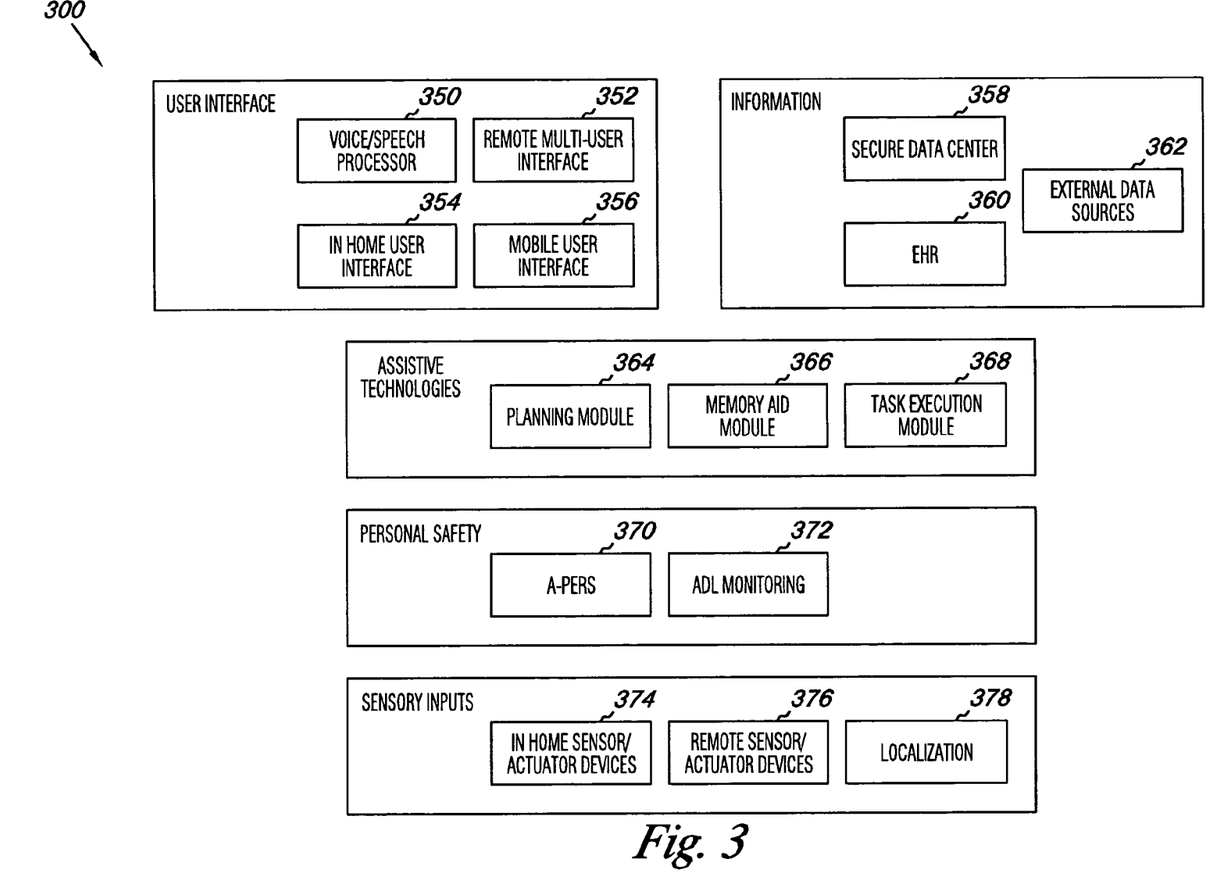
FIG. 3 illustrates an embodiment of a task performance monitoring system.

FIG. 3 illustrates an embodiment of a task performance monitoring system. In the embodiment of FIG. 3, a number of functionalities that are provided by the system 300 are illustrated. These functionalities are grouped as user interface functions, data storage and access functions, assistive technologies functions, personal safety functions, and sensory input functions. Embodiments can utilize more or less functions and/or function types, than are shown in the embodiment of FIG. 3.

With respect to user interface functions, a system and/or device can include, for example, a speech processor 350, a remote multi-user interface 352, an in home user interface 354, and/or a mobile user interface 356.

In various embodiments, such as that illustrated in FIG. 3, a system or device can include a data center 358, external health resources 360, and data sources 362.

With respect to assistive technologies functionality, embodiments can include a planning module 364, a memory aid module 366, and/or a task execution module 368.

In various embodiments, such as that illustrated in FIG. 3, a system or device can include personal safety functions such as automated personal emergency response system (a-pers) 370 and/or activities of daily living monitoring 372.

With respect to sensory input functionality, embodiments can include in home sensor devices 374, remote sensor devices 376, and localization devices 378. The sensory input functions can be utilized to collect information about the individual being monitored and/or be used in determining whether a task has been performed and/or performed successfully. As used herein, in home sensor devices are devices that are positioned within the dwelling in which the individual is being monitored. Remote sensor devices are those located outside the dwelling of the individual. These may be portable or fixed and, if portable, may be used within the dwelling, in some situations.

Localization devices, are used to determine the location of the individual. Examples, of localization devices that would be suitable for use in embodiments of the present disclosure are mobile communication devices (e.g., capable of positioning based upon proximity to one or more fixed receivers), and global positioning system (GPS) devices. Mobile phones and other portable devices can have such capabilities.

Figure 4:
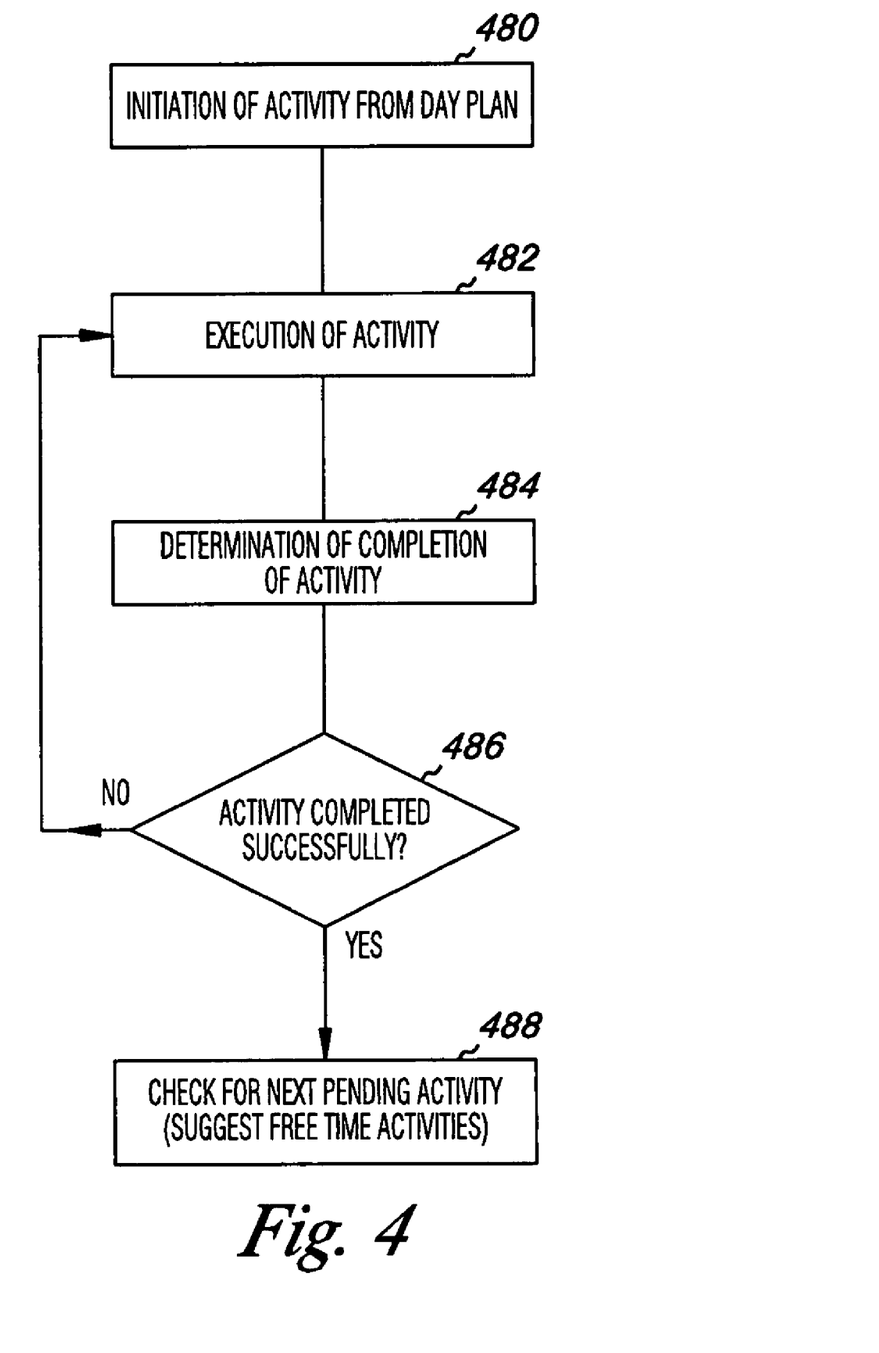
FIG. 4 illustrates an embodiment of a task performance planning, execution, and validation framework for use with various embodiments of the present disclosure.

FIG. 4 illustrates an embodiment of a task performance planning, execution, and validation framework for use with various embodiments of the present disclosure. In the embodiment of FIG. 4, the embodiment includes initiation of an activity from a day plan at 480.

The initiation of the activity (e.g., task or step) can, for example, be the monitoring of an activity that is being started by the individual being monitored, or the initiation of one or more instructions to aid in instructing the individual how to accomplish the activity. For example, in some embodiments, the instructions can be delivered in text, image, video, and/or audio information provided to the individual. This can be accomplished through the use of one or more files saved in memory and executable instructions that are executed to display the one or more files for the individual.

In some embodiments, the system can be designed such that the individual can select which format or formats the instructions are presented to them. For instance, the individual may select that the instructions are to be presented in text form or in video form when available, among other format selection choices. In some embodiments, the selection can be made by a user, such as an administrator or the manufacturer.

At block 482, the embodiment includes execution of the activity. The embodiment includes determination of completion of the activity, at block 484. In the embodiment of FIG. 4, the embodiment includes a verification that the activity has been successfully completed at block 486.

In some embodiments, an announcement can be made to the individual at various times during such processes as, for example, illustrated in FIG. 4. For instance, an announcement signaling the completion of a task or activity can be provided in one or more formats such as text, image audio, or video.

The method embodiment of FIG. 4 also includes checking for the next pending activity or other item on the day plan. This can be beneficial in moving the individual to a next task/step once the current task/step has been completed.

Figure 5:
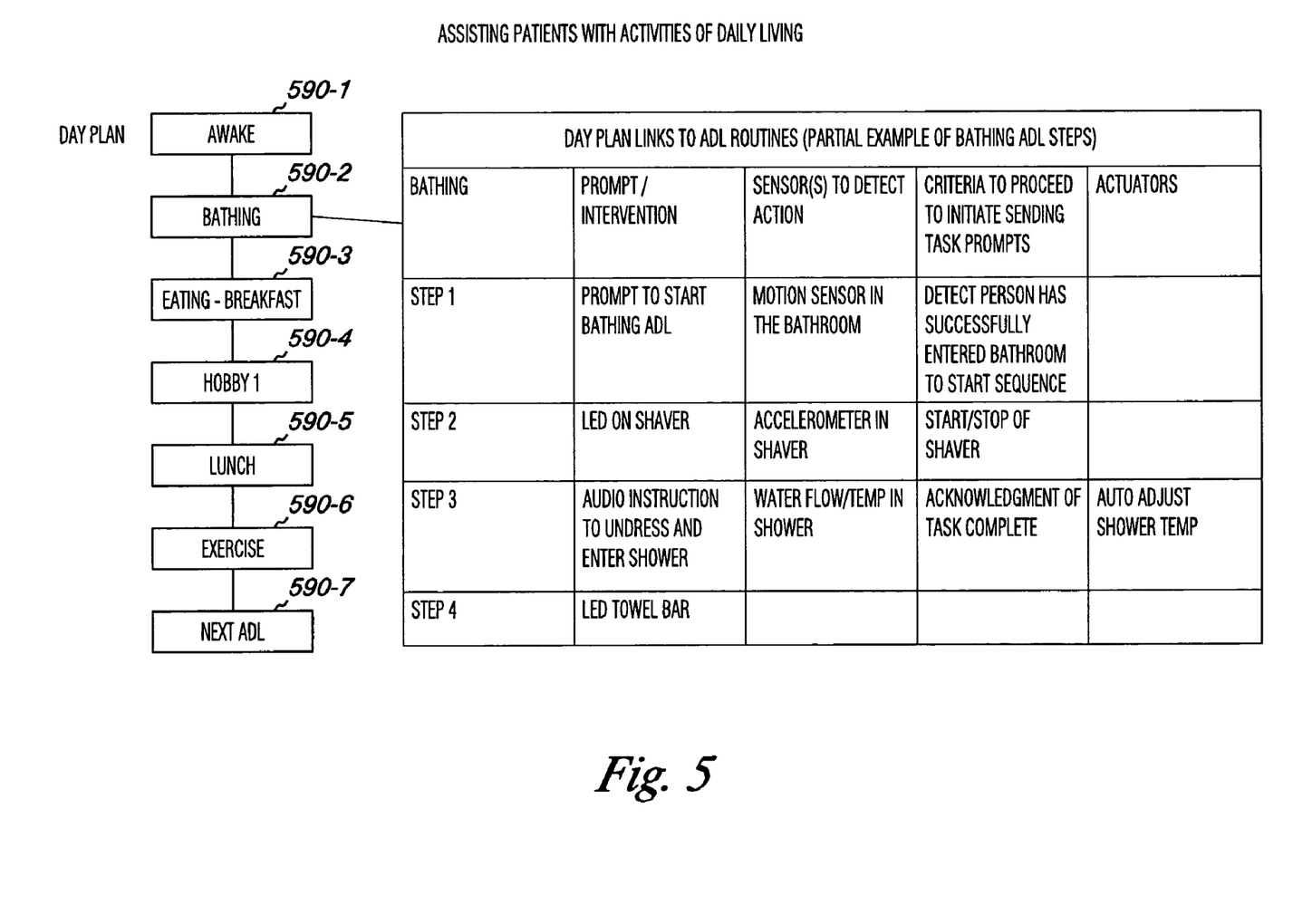
FIG. 5 illustrates task prompting routine for use with various embodiments of the present disclosure.

FIG. 5 illustrates task prompting routine for use with various embodiments of the present disclosure. In this Figure a number of tasks are identified, namely, the day plan includes waking 590-1, bathing 590-2, eating breakfast 590-3, performing a planned leisure activity (hobby) 590-4, eating lunch 590-5, exercise 590-6, and other activities of daily living 590-M.

Additionally, the bathing activity is further defined in the table to the right. In the table, an example of the steps and sensing methodology, criteria for proceeding, and actuations, if any, are discussed. This example provides a number of different steps of a task, a number of different sensor types used individually and in combination, different types of criteria for completion of the steps and/or task, among other features.

For instance, in the table, the first row includes the headings of the different information sections of the table. The headings are PROMPT/INTERVENTION, SENSOR(S) TO DETECT ACTION, CRITERIA TO PROCEED TO INITIATE SENDING TASK PROMPTS, AND ACTUATORS. The first column indicates the various steps for the Bathing Activity of Daily Living (ADL). In Step 1, the prompt is a prompt to indicate that the individual is to start their bathing task. The sensor to detect action is a motion sensor in the bathroom. The criterion is to detect that the individual has successfully entered the bathroom.

In step 2, the prompt is a light emitting diode (LED) on the shaver indicating to the individual that they are to use the shaver. The sensor used is an accelerometer in the shaver. The criteria are the starting and/or stopping of the shaver.

In step 3, an audio instruction is provided to the individual that indicates that they are to undress and enter the shower. A water flow sensor and/or temperature sensor is used in this example to detect action. The criterion is an audible acknowledgement from the individual that the task has been completed and an auto adjustment of the shower temperature can be made by an actuator during this step of the task.

In step 4, an LED on the towel bar indicates that the individual should take the towel off the towel bar. In this example, some instructions were provided at a high level and others were provided at a low level. This example, indicates the versatility that can be provided to an individual based upon the implementation of embodiments discussed herein.

As discussed herein, if no response is obtained from the individual, then the executable instructions can determine which third party to contact. Other sensors can be used in combination with, or instead of, a sensor worn by the individual to determine whether the individual is within the dwelling. Examples of other sensors include, motion sensors, sensors on the interior/exterior/garage doors, sensors on the individual's automobile, and the like.

Although specific embodiments have been illustrated and described herein, those of ordinary skill in the art will appreciate that an arrangement calculated to achieve the same techniques can be substituted for the specific embodiments shown. As one of ordinary skill in the art will appreciate upon reading this disclosure, various embodiments of the invention can be performed in one or more devices, device types, and system environments including networked environments.

Combination of the above embodiments, and other embodiments not specifically described herein will be apparent to those of skill in the art upon reviewing the above description. The scope of the various embodiments of the disclosure includes other applications in which the above structures and methods can be used. Therefore, the scope of various embodiments of the disclosure should be determined with reference to the appended claims, along with the full range of equivalents to which such claims are entitled.

In the foregoing Detailed Description, various features may have been grouped together in a single embodiment for the purpose of streamlining the disclosure. This method of disclosure is not to be interpreted as reflecting an intention that the embodiments of the invention require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method for monitoring task performance, comprising:
providing a number of sensors for monitoring an individual in performing a number of tasks from a list of tasks to be completed, wherein the number of tasks each include an associated number of steps to be completed by the individual;
initiating a first task based upon integrating sensor data provided by at least one of the number of sensors upon an activation of at least one of the number of sensors by the individual, wherein performing the first task includes the activation of at least one of the number of sensors by the individual and wherein the first task is commenced by the individual via the activation of at least one of the number of sensors by the individual;
monitoring the performance of a first task from the list by using at least one of the number of sensors and a timer;
providing the individual with a number of step instruction prompts associated with the steps of the first task;
obtaining task performance information corresponding to the performance of the first task by the individual, wherein the task performance information includes:
step prompt information including the number of step instruction prompts provided during performance of the first task;
timer data relating to the amount of time elapsed during performance of the first task; and
sensor data from the at least one of the number of sensors; and
adjusting the list of tasks to be completed based on the task performance information of the first task.

2. The method of claim 1, wherein adjusting the list of tasks includes changing the number of tasks from the list of tasks to be completed.

3. The method of claim 1, wherein adjusting the list of tasks includes changing the number of steps associated with the first task.

4. The method of claim 1, wherein providing the number of sensors includes:
providing a number of fixed sensors; and
providing at least one portable sensor.

5. The method of claim 4, wherein monitoring the performance of the first task includes using the at least one portable sensor to determine whether the first task is being completed.

6. The method of claim 1, wherein the method includes prompting the individual to perform a second task from the list when the first task has been completed.

7. The method of claim 1, wherein providing the individual with a number of step instruction prompts includes providing the individual with a reminder when a step of the first task remains uncompleted.

8. The method of claim 1, wherein the method includes prompting the individual via a mobile device.

9. The method of claim 1, wherein the method includes scheduling the number of tasks to be completed by the individual, the number of tasks to be completed in a sequential order.

10. A method for monitoring task performance, comprising:
providing a number of sensors and a timer for monitoring an individual in performing a number of tasks from a list of tasks to be completed, wherein the number of tasks each include an associated number of steps to be completed by the individual;
initiating a first task having an associated number of steps based upon integrating sensor data provided by at least one of the number of sensors upon an activation of at least one of the number of sensors by the individual and one or more context items, wherein performing the first task includes the activation of at least one of the number of sensors by the individual and wherein the first task is commenced by the individual via the activation of at least one of the number of sensors by the individual;
monitoring the performance of the first task by using at least one of the number of sensors and the timer; and
providing a task completion indication based upon a determination of completion of the first task.

11. The method of claim 10, wherein initiating the first task based upon one or more context items includes initiating the first task based upon one or more context items from the group including:
a time of day;
a day of the week;
a list of completed tasks;
a list of uncompleted tasks;
a completion status of a particular task; and
a determined location of the individual.

12. The method of claim 10, wherein initiating the first task based upon one or more context items includes initiating the first task based upon localizing the individual within a residence by using at least one fixed sensor located in the residence.

13. The method of claim 10, wherein the method includes initiating a second task having an associated number of steps to be completed based upon one or more context items.

14. The method of claim 10, wherein monitoring the performance of the first task by using at least one of the number of sensors includes using at least one portable sensor worn by the individual.

15. The method of claim 14, wherein monitoring the performance of the first task includes using the at least one portable sensor to determine whether the first task is being completed.

16. The method of claim 10, wherein initiating the first task includes prompting the individual on an interface of a mobile device.

17. The method of claim 10, wherein the method includes initiating the first task based upon integrating sensor data provided by at least one fixed sensor and at least one portable sensor.

18. The method of claim 10, wherein the method includes monitoring the performance of the first task by using integrated sensor data provided by at least one fixed sensor and at least one portable sensor.

19. A system for monitoring task performance, comprising:
- a number of fixed sensors located throughout a residence of an individual;
- at least one portable sensor worn by the individual; and
- a computing device in communication with the number of fixed sensors and the at least one portable sensor, the computing device including a memory having instructions storable thereon and executable by a processor thereof to perform a method that includes:
  - initiating a first task based upon integrating sensor data provided by at least one of the number of sensors upon an activation of at least one of the number of sensors by the individual, wherein performing the first task includes the activation of at least one of the number of sensors by the individual and wherein the first task is commenced by the individual via the activation of at least one of the number of sensors by the individual;
  - monitoring, by using at least one of the number of sensors and a timer, the performance of the first task from a list of tasks to be completed, wherein the number of tasks each include an associated number of steps to be completed by the individual;
  - providing the individual with a number of step instruction prompts corresponding to the associated number of steps of the first task;
  - obtaining task performance information corresponding to the performance of the first task by the individual, wherein the task performance information includes:
    - step prompt information including the number of step instruction prompts provided during performance of the first task;
    - timer data relating to the amount of time elapsed during performance of the first task; and
    - sensor data from the at least one of the number of sensors;
  - indicating that a particular step has been completed based on the sensor data; and
  - adjusting, based on the task perfoi ance information corresponding to the performance of the first task, the number of step instruction prompts provided to the individual in performing the first task on a subsequent occasion.

20. The system of claim 19, wherein indicating that a particular step has been completed is accomplished by placing a flag in a data file.

21. The system of claim 19, wherein adjusting the number of step instruction prompts provided to the individual in performing the first task on a subsequent occasion is accomplished via a user interface.

22. The system of claim 19, wherein adjusting the number of step instruction prompts provided to the individual in performing the first task on a subsequent occasion is accomplished via an interface usable by the individual being monitored.

23. The system of claim 19, wherein the system includes instructions to analyze the task performance information and initiate adjusting the number of step instruction prompts provided to the individual in performing the first task on a subsequent occasion.

24. The system of claim 19, wherein the system includes instruction to schedule the number of tasks to be completed by the individual.

25. The system of claim 19, wherein the system includes a guidance module for providing guidance information for accomplishing at least one step.

26. The system of claim 19, wherein the system includes a tracking module for tracking completion of the steps associated with at least one task.

27. The system of claim 19, wherein the system includes an emotion sensing module.

28. The system of claim 19, wherein the system includes a solution module to provide information to the individual to aid in solving a particular problem encountered by the individual.

29. The system of claim 28, wherein the solution module includes instructions executable to assist the individual with locating a particular item by providing the individual with a number of possible locations of an item.

30. The system of claim 29, wherein the number of possible locations is based on data from at least one of the number of fixed sensors.

31. The system of claim 29, wherein the number of possible locations is based on data from a database.

32. The system of claim 19, wherein adjusting the number of step instruction prompts provided to the individual in performing the first task on a subsequent occasion includes reducing the number of step instruction prompts provided to the individual in performing the first task on the subsequent occasion.

33. The system of claim 19, wherein adjusting the number of step instruction prompts provided to the individual in performing the first task on a subsequent occasion includes increasing the number of step instruction prompts provided to the individual in performing the first task on the subsequent occasion.

* * * * *